(12) United States Patent
Wiscovitch et al.

(10) Patent No.: US 10,390,529 B2
(45) Date of Patent: Aug. 27, 2019

(54) EMULSION BLOCKING LATEX PROTEIN AND OTHER SKIN IRRITANTS

(71) Applicant: BIOTD SOCIEDAD ANÓNIMA, Heredia (CR)

(72) Inventors: Robin A. Wiscovitch, Atenas (CR); Juan Valdes Gonzalez, Heredia (CR); Roy Mora Gonzaga, San José (CR)

( * ) Notice: Subject to any disclaimer, the term of this patent is extended or adjusted under 35 U.S.C. 154(b) by 0 days.

(21) Appl. No.: 15/314,239

(22) PCT Filed: May 26, 2014

(86) PCT No.: PCT/CR2014/000002
§ 371 (c)(1),
(2) Date: Nov. 28, 2016

(87) PCT Pub. No.: WO2015/180696
PCT Pub. Date: Dec. 3, 2015

(65) Prior Publication Data
US 2017/0188576 A1 Jul. 6, 2017

(51) Int. Cl.
| | | |
|---|---|---|
| A61K 8/02 | (2006.01) | |
| A61K 8/19 | (2006.01) | |
| A61K 8/41 | (2006.01) | |
| A61K 8/92 | (2006.01) | |
| A61K 9/00 | (2006.01) | |
| A01N 25/04 | (2006.01) | |
| A01N 25/24 | (2006.01) | |
| A01N 25/30 | (2006.01) | |
| A01N 33/12 | (2006.01) | |
| A01N 37/10 | (2006.01) | |
| A01N 59/16 | (2006.01) | |
| A01N 65/28 | (2009.01) | |
| A61B 17/00 | (2006.01) | |
| A61B 42/00 | (2016.01) | |
| A61K 33/38 | (2006.01) | |
| A61K 47/44 | (2017.01) | |
| A61K 8/368 | (2006.01) | |
| A61K 9/107 | (2006.01) | |

(52) U.S. Cl.
CPC ............ *A01N 25/24* (2013.01); *A01N 33/12* (2013.01); *A01N 37/10* (2013.01); *A01N 59/16* (2013.01); *A01N 65/28* (2013.01); *A61B 42/00* (2016.02); *A61K 8/0241* (2013.01); *A61K 8/19* (2013.01); *A61K 8/368* (2013.01); *A61K 8/41* (2013.01); *A61K 8/922* (2013.01); *A61K 9/0014* (2013.01); *A61K 9/107* (2013.01); *A61K 33/38* (2013.01); *A61K 47/44* (2013.01); *A61B 2017/00889* (2013.01); *A61B 2017/00893* (2013.01); *A61K 2800/413* (2013.01)

(58) Field of Classification Search
None
See application file for complete search history.

*Primary Examiner* — David J Blanchard
*Assistant Examiner* — Sarah J Chickos
(74) *Attorney, Agent, or Firm* — Fox Rothschild LLP

(57) ABSTRACT

The present invention relates in general to a medical device consisting of a blocker made of a mixture of natural products such as African palm oil and the triglycerides thereof and natural waxes as active and emulsifying components, polymer and silver nanoparticles, acting as a blocker for latex protein and other skin irritants.

6 Claims, No Drawings

EMULSION BLOCKING LATEX PROTEIN AND OTHER SKIN IRRITANTS

FIELD OF THE INVENTION

The present invention relates in general to a medical device consisting of a blocker made of a mixture of natural products, such as African palm oil and the triglycerides thereof, and natural waxes as active and emulsifying components, polymer and silver nanoparticles, acting as a blocker for latex protein and other skin irritants.

BACKGROUND OF THE INVENTION

Latex allergy represents a real problem of public health worldwide, and, despite multiple efforts to solve this situation, no other substitute material having the same characteristics that made latex a successful product has been discovered to date. However, thanks to biotechnology based on surface chemistry and microfilm technology, the present invention succeeds in providing a solution to this condition.

The latex products industry uses about 4.5 million tons of latex per year (5). This material is used in the manufacture of rubber pumps, condoms, electrical materials, gloves and other products for medical use. This polymer is related to many daily activities of health personnel, especially when using gloves or disposable medical materials (1, 2)

Latex is the second most common cause of anaphylactic reaction in operating rooms (16.6% of cases). However, the incidence has declined in response to the identification of patients at risk, improvements in laboratory determinations, and introduction of measures for the prevention and reduction of latex in many medical products.

The prevalence of sensitization to latex is less than 1% in the normal population without atopy, but in health personnel it fluctuates between 3 and 12%. (6, 9, 11)

Using the determination of IgE in serum (specific against latex), 4-6.4% of individuals are positive (14). The incidence of latex sensitization (measured as a level of specific IgE) in ambulatory surgical patients is 6.7% (9). The prevalence of latex allergy in the general population is 0.7-11%. (15)

In a group of non-sensitized individuals who began to work in health, it was demonstrated that there was a 6.4% cumulative incidence of skin sensitivity, 1.8% for people with rhinoconjunctivitis, and 4, 5% for those with occupational asthma. (21)

High-risk latex allergy groups include: health workers, workers with occupational exposure to latex (police officers, stylists, food handlers), individuals with a history of atopy, and patients with spina bifida and genitourinary abnormalities requiring multiple surgical interventions. (9, 11, 16, 17)

Patients with spina bifida, even without multiple surgeries, are at increased risk. The most frequent manifestation in spina bifida is urticaria (8, 9, 18, 22). Obojski (23) reported respectively 32.4% and 18.8% prevalences in boys and girls when sensitized and suffering from allergy to latex. In children with spina bifida and congenital diseases requiring multiple surgeries, the frequency is reported to be between 23-70% (10, 17, 18, 22).

Health workers are the main risk group due to constant exposure to latex products; the frequency of sensitization in the hospital population fluctuates between 2.8-17%. In other occupations with latex exposure, the frequency ranges from 5-11%. Allergy in health workers with latex allergy is 2.2-4.2 times more frequent than in control workers. In adults with latex allergy, a prevalence of up to 82% is reported (17). A health worker who is atopic has an increased risk of sensitization and allergy to latex.

Anesthesiologists have a 12.5% and 2.4% prevalence of sensitization and allergy to latex respectively (23). Anesthesiologists treating adults change their gloves more often than those treating children and have a higher sensitivity to latex, those affected being estimated to be 24%. (9, 24)

Although the latex industry has tried to solve the problem of allergies, this has not been achieved by any technique, including: talc treatment, multiple washes, chlorination, hydrogel treatments, PVC gloves, neoprene gloves, Styrene block copolymer gloves, and even polyurethane gloves. But none of these managed to even lessen the problem.

The other materials that are currently available have not been able to reproduce the main benefits of latex, which are price, sensitivity, durability, and memory that keeps the gloves shape when they stretch, even with the most demanding maneuvers.

Latex protein: Natural latex is a milky liquid from the *Hevea Brasiliensis* tree. Its matrix contains soluble and insoluble proteins. These proteins are subjected to hydrolysis and denaturation during the manufacturing process. The latex particles are insoluble in water, but the presence of ammonium that is used to stabilize them and preserve them increases their solubility. The ammonium breaks the organelles present in the latex and releases the soluble material. Fragments of the proteins give rise to low molecular weight polypeptides. About 240 different polypeptides have been detected in the ammoniated latex, with molecular mass between 5-200 kd. However, only 25% of these peptides, with molecular mass between 5-100 kd, show ligation with IgE of the serum of patients with latex allergy. (7, 9, 11)

The main allergen in the latex is the rubber elongation factor (Hev b). There are 11 Hev b proteins (Hev b1 to Hev b11) within these Hev b5 (18-20 kd) or latex profilin and Hev b6.02 (4.7 kd) hevein. Sensitization to Hev b5 is common in the health worker group. The concentration of Hev b1 in natural rubber products is reported to be between 18-40 mg/g, corresponding to 2-4% of extractable total protein in the gloves. Hev b6.02 and Hev b5 are responsible for most latex allergens in medical gloves. (9, 11, 12, 15, 17, 25)

Latex allergens interact with carbohydrates. These allergens, such as Hev b6.01, Hev b6.02 and Hev b11, are bound to oligosaccharides of N acetylglucosamine thanks to a hevein domain. This type of domain has also been described in other plants, notably Pers a 1 (avocado), and some others present in banana, kiwi and chestnut, which could explain the fact that people sensitive to latex are also sensitive to these fruits. (20)

Corn starch, used as a powder to lubricate gloves, acts as an allergen transporter when linked to latex proteins. When the particles are aerolized upon use of the gloves, exposure to latex occurs in all individuals in the area. (13) Corn starch powder adheres to latex particles and acts as a carrier. Talc (magnesium silicate) is capable of binding latex particles, however the union is irreversible as they cannot release the latex to the environment and it is a bad aeroallergen transporter for being heavier.

Another exposure route is the one that occurs when the allergens of the latex come into contact with the tissues and mucous membranes of the patient during surgical, dental or medical procedures. (13)

Sensitivity to latex: In the molecular structure of allergenic proteins, there are immunodominant regions, called epitopes, which interact with the antigen-binding fragments (Fab) of the specific IgE antibodies. Fab-allergen immune complexes have between 15 and 22 amino acid residues. Of these, only 3 to 5 residues contribute to the binding process through multiple non-covalent complementary bonds, originated by electrostatic forces, mainly Van der Waals type. (19)

Patients with latex sensitivity have an altered humoral and cellular immune response, which facilitates the reaction with environmental antigens.

Increase of serum IgE: In 80% of the cases, IgE is capable of mediating an immediate, but also a late, immunological response (FIG. 1). (20)

Surface Chemistry can be more or less defined as the study of chemical reactions at interfaces. It is closely related to surface engineering, whose purpose is to modify the chemical composition of a surface by incorporating certain elements or functional groups that produce various desired effects or improvements in the properties of the surface or interface. Surface Chemistry also overlaps with electrochemistry. Surface science is of particular importance for the field of heterogeneous catalysis.

The adhesion of the gas or liquid molecules to the surface is known as adsorption. This may be due to chemical absorption or porphyrosorption. These are also included in Surface Chemistry.

The behavior of a solution based on the interface is affected by the surface charge, dipoles, energies, and their distribution within the double electric layer.

Surface Chemistry develops and offers superior low cost products formulated for the preparation of specialized surfaces and difficult surface cleaning applications. These new chemicals are used in the preparation and manufacture of high technology devices; however, their usefulness also extends to cleaning industrial surfaces and preparation. Chemical surface discoveries can help achieve the most effective surface preparation, textures and cleaning needs of the solar cell and the manufacture of semiconductors.

Surface Chemistry consists of the study of the physical and chemical processes that take place in the interfaces of the different habitual states of matter: solids, liquids and gases. That is, it deals with the contact zones between the different states of matter or phases where a set of atoms, small in quantity of species in comparison with the total of atoms and molecules that constitute the phases, interacts and form new chemical species. Therefore, Surface Chemistry must cover the basic concepts of Solid State Chemistry and Coordination Chemistry.

The interest of Surface Chemistry, as an interdisciplinary field of investigation, lies in the multiple applications and consequences derived from the processes that take place on surfaces, among which we can mention: electrochemical reactions, colloidal systems, detergency and flotation, biological membranes, lubrication, corrosion, heterogeneous catalysis, etc. Limiting us to the application of the concepts of Surface Chemistry in Heterogeneous Catalysis, we must remember several key facts in relation to history and industrial applications. Thus, it is revealing that, in the third decade of the nineteenth century, when J. J. Berzelius or M. Faraday began to write about the phenomenon of "catalysis", they referred to a previous patent of 1831 consisting of a heterogeneous catalytic process, the manufacture of sulfuric acid.

No less important is another development of catalysts, this one from the beginning of the 20th century, which facilitated the ammonia synthesis using atmospheric nitrogen as reagent. This industrial process made possible the production of fertilizers and the advent of modern agriculture, which, among other things, made it possible to feed an exponentially growing world population over the past century. We could delve into how the oil derivatives industry, based on various catalytic processes, has helped in the expansion of automotive or aviation use.

Also, the plastics, produced with polymerization catalysts of organic compounds, are now present in all the materials that surround us. And from all this we can conclude that catalysis, and therefore Surface Chemistry, can be considered as technological pillars of the chemical industry and as key concepts in the resolution of new environmental and energetic problems. From a final point of view, Surface Chemistry and its heterogeneous catalysis are present in new industrial and technological developments ranging from the production of hydrogen or the transformation of biomass to photocatalysis, through fundamental operations to achieve a more sustainable chemical industry (Green Chemistry). The research situation in Surface Chemistry is exciting.

The emergence of new techniques of study, the evolution of experimental analytical methods and the support of computational methods have meant going from mere speculations about the nature of the surface centers where a process or reaction takes place to being able to achieve a rational design of the synthesis of the catalytically active material (we would now call it nanomaterial). As for the challenges applied, catalytic reactions leading to enantiomers may have special appeal, since they require atomic-scale control of both the surface of the catalyst and the intermediate species that are being produced; that is, of the intermediates chemisorbed or bound to the surface site with chiral specificity.

From the point of view of the deep knowledge of the reactions that occur on a surface, we must emphasize the development of the techniques with temporal resolution in the detection of the chemical changes, that is to say those that allow us to follow the intermediates present in the surface for periods of the order of the microsecond (10-6 seconds) up to the PS (10-12 seconds) depending on the life span of the species and the concrete reaction studied.

By way of example, we can indicate the spectroscopies of absorption of X-rays capable of giving rise to spectra in a few microseconds. It is also necessary to mention the studies that are carried out using isotopically labeled compounds, in particular if they are operated in the modern Temporal Analysis of Products (TAP) reactors. Many of these experimental techniques are performed "in situ", that is, while studying the chemistry under the conditions of the reaction that is taking place.

DETAILED DESCRIPTION OF THE INVENTION

The present invention consists of an emulsion made with silver nanoparticles which functions as a latex protein and other skin irritants blocker. The blocking process is based on the behavior of a solution based on the interface that is affected by the surface charge, dipoles, energies, and their distribution within the double electric layer. The contact zones between the different states of matter or phases where a set of atoms, small in quantity of species in comparison with the total of atoms and molecules that constitutes the phases, interacts while forming chemical bonds.

For example, several processes take place on surfaces, among which we can mention: electrochemical reactions, colloidal systems, detergency and flotation, biological membranes, lubrication, corrosion, heterogeneous catalysis, etc.

The invention uses microfilm technology and refers to an application of surface chemistry with the final modification or protection of a surface where a microfilm is generated with the bonding of chemical bonds between the polymers, the treacylglycerides generating a microfilm.

This invention is an emulsion based on silver nanoparticles, very effective for blocking latex protein and other skin irritants and thereby preventing it from contacting and affecting the skin by producing a kind of invisible glove. This device allows the use of the properties of silver as a protective barrier that blocks the latex protein, being an antibacterial protective barrier for people working with their hands on risk surfaces such as patients' skin, food or money, thereby maximizing the properties of silver to cure recurrent skin diseases and avoiding bacterial contact.

It is an aqueous suspension of lipids with a high degree of saturation that has a protective waxing effect, where alkali salts of the fatty acids associated with methylvinylether copolymer and silver nanoparticles generate an impenetrable film.

The mixture of the alkali salts of the fatty acids present in these lipids blocks the penetration of irritants such as latex protein or irritants.

It is a product intended to solve the number one problem of the latex glove industry that is the cutaneous allergic reaction caused by the latex protein.

There is a precedent in Costa Rica, widely publicized in the press, in which the Constitutional Chamber through sentence No. 2003-1432 (4) forced the Costa Rican Social Security Fund to indemnify and provide a solution to a surgeon with a known sensitivity to latex. At that time, the only solution that the Social Security could offer is the supply of gloves of another material in spite of being more expensive and difficult to obtain.

This invention is a biotechnological solution, through the application of surface chemistry and microfilm technology, made with natural products from our land (one of which is a waste of the Costa Rican industry). The formula is applied to the skin, producing a barrier that prevents proteins in the latex from reaching or affecting the skin.

The reason and basis that led to the preparation of this invention is the risk of developing allergy to latex, by all those users, continuously exposed to this allergen, due to their type of work. Many of these workers are unable to carry out their work since they are inevitably no longer able to use this type of gloves. For these reasons, this invention is a solution that solves this problem.

Thanks to its formulation, a mixture of natural products provided by triglycerides as active component, natural waxes and emulsifiers, forms a microfilm on the epidermis, blocking by interaction the transfer of proteins from the latex to the skin, and prevents the development of allergy: without any effect on the dermis and all its usefulness is applicable to this allergen. It is also non-toxic and does not pollute ecosystems.

In addition to its use to prevent the development of latex allergy, the invention may block the action of irritants on the skin, such as chemicals, for example formalin, xylol, cement, or household substances such as dishwashing soaps.

The product is born in nanotechnology and is especially effective due to its particle size that will allow better results unlike what exists in the state of the art. Ionic silver, when near a virus, fungi, bacteria or any other unicellular organism, neutralizes the enzymes that they use to metabolize the oxygen, at the same time that they alter the permeability of the membrane of the unicellular organism. In a few minutes, these organisms are effectively asphyxiated. It is also known that ionic silver does not act on the cells of the host, as the enzymes are radically different from those of unicellular organisms. Similarly, silver acts as a neutralizer of the latex protein, creating a barrier that protects the skin.

It is the only product on the world market that solves the allergy produced by latex gloves. It is a white suspension, consisting of natural products such as vegetable oils, fatty acids from vegetable oils, essential oils, emulsifiers and thickeners. Especially manufactured to block the antigens contained in latex products, especially those of the latex glove, so that it does not reach the wearer's skin, while moisturizing the skin and allowing it to heal through its own natural processes. Most allergies will heal in 4 days and more sensitization will be prevented, as long as the user continues to block allergens with the present invention.

The invention thus blocks the direct contact of the latex materials [gloves, etc.] with the skin and therefore eliminates the inherent adverse allergic effect of the latex protein. It directly controls latex allergies, both type 1 and type 4, is 100% effective, prevents users [not yet sensitized] from any future sensitization and avoids problems of workforce disabilities due to the dreaded latex allergy. It is a product that uses microfilm technology and surface chemistry. It is 100% safe as a result of a formulation that consists of natural active ingredients and presents a moisturizing and breathable barrier that promotes optimal natural conditions to accelerate healing, has no known side effects, fast acting allergies to latex type 1 are resolved within a week and the microfilm technology, with which the present invention is formulated, enables close monitoring of the skin contours. It is the only one of its kind, which allows glove users to cope with latex allergies and has additional benefits because it protects users from the effects of harsh chemicals on the skin.

Composition. The composition of the product is detailed below:

1.1. Stock Solution

| | |
|---|---|
| Water | 88.2% |
| Sodium hydroxide | 0.35% |
| Vegetable oil of palm oil | 5.45% |
| Parafan | 5.10% |
| Triton x 100 | 0.42% |
| Triethanol amine | 0.42% |
| Sodium benzoate | 0.06% |

1.2. Commercial Solution

| | |
|---|---|
| Stock solution | 10.0% |
| Gantrez AN 139 | 1.0% |
| *Eucalyptus* | 0.5% |
| Dissolution with silver nanoparticles (5 ppm) | 98.5% |

2. Materials section. The materials used in the composition are as follows:
Asian Palm Oil.
Parafan, mixtures of vegetable fatty acids of vegetal origin, produced as a result of its process of manufacture and the purification of African palm oil.
Industrial grade sodium hydroxide.
Industrial grade sodium benzoate.
Gantrez AN 139.
Triton x 100 whose active component is Nonyl phenol ethoxylate, which is used in the product as an emulsifier.
Water. Deionized water
Triethanolamine: Industrial grade amine.
ASTEK Eucalyptus, code P0150 or similar.

Silver nanoparticles in deionized water. (Ag). These silver nanoparticles are low concentrations suspended in distilled water and produced by electric methods from silver electrodes having an atomic mass of 107.868 g/mol, melting point of 960.5° C., boiling point of 2000° C. and density at 15° C. of 10.49 g/mL. It is not attacked by water or atmospheric oxygen; it is obscured by ozone and hydrogen sulfide. It is inert to many acids, reacts easily with diluted nitric acid and hot sulfuric acid. It is not sensitive to light in metallic form.

Generator of silver nanoparticles. The generator used is a Robey device which uses a voltage source of 110-115 V and comprises a current controller and produces silver nanoparticles in line. It comprises two silver electrodes, placed in a compartment, and a cellulose filter which restricts the passage of large particles of silver, letting through nanoparticles between 60 and 140 nm.

Preparation of the Stock Solution:

5.10 kg of Parafan are placed in a 150 L stainless steel vessel and heated until they are melted and 1 L of a sodium hydroxide solution containing 350 g of NaOH per liter is added slowly, then mixed until the Parafan is dissolved. 5.45 kg of African palm oil are added to this vessel, stirred and 420 g of triton X100 and 420 g of triethanolamine are then added. Water is added to make up to 100 L of solution and stirred to form a homogeneous white suspension and then 60 g of sodium benzoate is added, stirring until complete dissolution is achieved.

Commercial Solution:

87.2 L of water with silver nanoparticles are placed in a 150 L vessel and 10 L of stock solution is added under stirring and the mixture is stirred for 5 minutes and then 1.0 kg of Gantrez AN-139, which was prepolymerized in a stainless steel vessel containing 1 L of deionized water at 40° C. is added, and continuous stirring is applied until the product becomes clear and viscous. 500 ml of eucalyptus oil is added to this solution under stirring.

Physico-Chemical Specifications.

The physico-chemical specifications of the product are as follows:

Palm Oil.

This oil is characterized by a high content of short chain fatty acids of 12 carbons or less. It has a relatively low and marked melting point, and is quite hard and fragile at lower temperatures. Because palm kernel oil has a high content of C18 unsaturated acids, it can produce a broader range of products, after fractionation and/or hydrogenation. Some physico-chemical properties are shown in the following table.

Physico-Chemical Characteristics of Palm Oil:

| Specific weight | 0.925-0.935 |
| Melting point | 19-26° C. |
| Refraction point at 40° C. | 1.45-1.452 |
| Saponification point | 239-257 |
| Iodine content | 12-18 |

Soybean Oil.

Soybean oil is widely used in the preparation of refined products, although not as much as palm oil. Soybean oil has the characteristics shown in the following table.

| Density at 15° C. | 0.922-0.930 |
| Iodine content | 121-135 |
| Refractive index at 25° C. | 1.4729-1.4742 |
| Saponification index | 190-193 |
| Melting point | 27° C. |

Essence of Eucalyptus.

Formula: $C_{10}H_{18}O$, M.=154.24, CAS [470-82-6]

EC Number (EINECS): 207431-5

Appearance: Transparent, colorless liquid.

Odor: Characteristic.

Boiling point: 177° C.

Melting point: 1.5° C.

Flash point: 48° C.

Density (20/4): 0.924

Solubility: Immiscible with water.

Mechanism of Action of the Invention.

The present invention provides a major part of the replacement of the physiological lipids that are reduced in the stratum corneum in patients with atopic dermatitis (AD). In addition, it replenishes the skin with ceramide, a key lipid lacking in the corneal layer in patients with AD. The compound offers an optimal ratio of 3:1:1 ceramides, cholesterol and free fatty acids to help normalize the barrier function of the skin.

The invention acts by forming a vapor permeable barrier which allows a metabolic response to repair the skin and helps to normalize the pH in the stratum corneum.

This emulsion is readily reacted with diluted nitric acid and hot sulfuric acid; and it is not sensitive to light in the metallic form. In addition, sodium hydroxide or anhydrous caustic soda is used to neutralize the acids.

BIBLIOGRAPHY

Bibliographic References

1. Hepner D L, Castells M C. Latex allergy: an update. Anesth Analg 2003; 96: 1219-1229.
2. Ownby D R. A history of latex allergy. J Allergy Clin Immunol 2002; 110: S27-32.
3. Alenius H, Turjanmaa K, Palosuo T. Natural rubber latex allergy. Occup Environ Med 2002; 59: 419-424.
4. Constitutional Chamber of the Supreme Court of Justice. Judgment 2003-1432 (May 6, 2003).
5. Tesiorowski C C. Latex allergies in the health care worker. J Perianesth Nurs 2003; 18: 18-31.
6. Turjanmaa K. Diagnosis of latex allergy. Alergy 2001; 56: 810-812.
7. Quirce S, Olaguibel J M, Alvarez M J, Tabar A I. El latex. Un importante aeroalergeno implicado en el asma ocupacional. An sis sanit Navar 2003; 26: S81-95.
8. Zucker-Pinchoff B. Latex allergy. Mt Sinai J Med 2002; 69:38-95.
9. Karisola P, Alenius H, Mikkola J, Kalkkinen J, Kalkkinen N, Helin J, et al. The major conformational IgE-binding epitopes of hevein (hev b6.02) are identified by a novel chimera based allergen epitope mapping strategy. J Biol Chem 2002; 277: 22656-22661.
10. Lundberg M, Wrangsjo K, Johansson S G O. Latex allergy from glove powder an unintended risk with the switch from talc to cornstarch. Allergy 1997; 52: 1222-1228.
11. Lavaud F, Prevost A, Cossart C, Guerin L, Bernard J, Kochman S. Allergy to latex, avocado pear, and banana: evidence for a 30 kd antigen in immunoblotting. J Allergy Clin Immunol 1995; 95: 557-564.

12. Sicherer S H. Clinical implications of cross-reactive food allergens. J Allergy Clin Immunol 2001; 108: 881-890.
13. Aalberse R C, Akkerdaas J H, van Ree R. Cross-reactivity of antibodies to allergens. Allergy 2001; 56: 478-490.
14. Heilman D K, Jones R T, Swanson M C, Yunginger J W. A prospective, controlled study showing that rubber gloves are the major contributor to the latex aeroallergen levels in the operating room. J Allergy Clin Immunol 1996; 98: 325-330.
15. Schwartz L B, Bradford T R, Rouse C, Irani A M, Rasp G, Van der Zwan J K, et al. Development of a new, more sensitive immunoassay for human tryptase: use in systemic anaphylaxis. J Clin Immunol 1994; 14: 190-204.
16. Patriarca G, Nucera E, Buonomo A, Del Ninno M, Roncallo C, Pollastrini E, et al. Latex allergy desensitization by exposure protocol: five case reports. Anesth Analg 2002; 94: 754-758.
17. Turjanmaa K, Kanto M, Kautiainen H, Reunala T, Palosuo T. Long-term outcome of 160 adult patients with natural rubber latex allergy. J Allergy Clin Immunol 2002; 110: S70-74.
18. Allmers H, Brehler R, Chen Z, Rauf-Heimsoth M, Fels H, Baur X. Reduction of latex aeroallergens and latex-specific IgE antibodies in sensitized workers after removal of powered natural rubber latex gloves in a hospital. J Allergy Clin Immunol 1998; 102: 841-846.
19. Charous B L, Schuenemann P J, Swanson M C. Passive dispersion of latex aeroallergens in a healthcare facility. Ann Alergy Asthma Immunol 2000; 85: 285-290.
20. Navarro, Elkin et al. Las proteinas alergenicas: un novedoso blanco para el desarollo de estudios en proteomica funcional. Salud Uninorte. Barranquilla (Col.) 2008; 24 (2): 303-318
21. Sastre Dominguez J. Latex Immunotherapia, En: Blanco Coverra C, Quirce Gancedo S (ed). Alergia al latex 2002. Sociedad Espanola de Alergia e Immunologia Clinica. Barcelona: MRA Editions; 2002: 247-252.
22. Fuchs T. Latex allergy. J Allergy Clin Immunol 1994; 93: 951-952.
23. Obojski A, Chodorski J, Barg W, Mdrala W, Fal A M, Malolepszy J. Latex allergy and sensitization in children with spina bifida. Pediatr Neurosurg 2002; 37: 262-266.
24. Allmers H, Brehler R, Chen Z, Rauf-Heimsoth M, Fels H, Baur X. Reduction of latex aeroallergens and latex-specific IgE antibodies in sensitized workers after removal of powered natural rubber latex gloves in a hospital. J Allergy Clin Immunol 1998; 102: 841-846.
25. Hosler D, Burkett S L, Tarkanian M J. Prehistoric polymers: rubber processing in ancient Mesoamerica. Science 1999, 284: 1988-1991.

The invention claimed is:
1. A silver nanoparticle composition in water, comprising 10.0% stock solution, 1.0% of a copolymer of methyl vinyl ether/maleic anhydride, 0.5% eucalyptus oil, and 88.5% solution with silver nanoparticles (5 ppm); wherein the stock solution consists of:
   a. 88.2% water;
   b. 0.35% sodium hydroxide;
   c. 5.45% African palm vegetable oil;
   d. 5.10% mixture of fatty acids of vegetable origin;
   e. 0.42% Polyoxyethylene octyl phenyl ether;
   f. 0.42% triethanol amine; and
   g. 0.06% sodium benzoate.
2. Composition of claim 1, wherein the water is distilled or deionized.
3. A composition of claim 1, wherein the African palm oil has the following characteristics:
   a. it has a specific weight of 0.925-0.935 g/ml;
   b. it has a melting point of 19-26° C.;
   c. it has a refraction point at 40° C. of 1.450-1.452;
   d. it has a saponification point of 239-257 mg/g;
   e. it has an iodine content of 12-18 g iodine/100 grams of product.
4. Composition of claim 1, wherein the sodium hydroxide is used to neutralize the mixture of fatty acids of vegetable origin.
5. A process for obtaining the composition of claim 1, which consists of the following steps:
   a. 100 liters of distilled or deionized water are poured into a stainless-steel container and a polyethylene hose connected to a water pump is inserted thereof;
   b. the water pump drives the water to the generator of the silver nanoparticles, which is connected to a voltage source of 110-115 Volts;
   c. the generator comprises a pump to control the amount of water entering the electrodes and another to regulate the amount of water leaving the system;
   d. with the second water pump, connected to a 110-115 V outlet, the water containing the silver nanoparticles in the system is recirculated for one minute to increase the concentrations of the silver particles and ensure that the final product contains the required silver nanoparticle concentrations;
   e. the controlled size of the nanoparticles is done through filtration;
   f. to the 98.5 L of water with silver nanoparticles contained in a sanitary grade stainless-steel container, 1 kg of polymerized copolymer of methyl vinyl ether/maleic anhydride is added under stirring, 10 liters of the stock solution and 500 ml of *Eucalyptus* oil, are added and stirred with a stainless-steel propellant, connected-to a ⅛ HP motor.
6. The process of claim 5, wherein the silver nanoparticle generator uses a voltage source of 110-115 V and comprises a current controller, two silver electrodes, and a cellulose filter, which lets through nanoparticles between 60 and 140 nm, and restricts the passage of silver nanoparticles larger than 140 nm and smaller than 60 nm.

\* \* \* \* \*